(12) United States Patent
Law

(10) Patent No.: US 8,591,971 B2
(45) Date of Patent: Nov. 26, 2013

(54) METHODS AND APPARATUS FOR PRODUCING PARTIALLY HYDROLYSED PROTEINACEOUS PRODUCTS

(75) Inventor: Roger W. Law, Tualatin, OR (US)

(73) Assignee: Axiom Scientific and Charitable Institute, Ltd., Tualatin, OR (US)

( * ) Notice: Subject to any disclaimer, the term of this patent is extended or adjusted under 35 U.S.C. 154(b) by 936 days.

(21) Appl. No.: 12/592,948

(22) Filed: Dec. 4, 2009

(65) Prior Publication Data

US 2010/0196538 A1    Aug. 5, 2010

Related U.S. Application Data

(60) Provisional application No. 61/120,027, filed on Dec. 4, 2008.

(51) Int. Cl.
| | |
|---|---|
| A23L 1/31 | (2006.01) |
| A23J 1/02 | (2006.01) |
| A47J 37/12 | (2006.01) |
| A47J 23/00 | (2006.01) |

(52) U.S. Cl.
USPC .................. 426/59; 426/657; 99/408; 99/537

(58) Field of Classification Search
None
See application file for complete search history.

(56) References Cited

U.S. PATENT DOCUMENTS

| | | |
|---|---|---|
| 2,350,811 A | 6/1944 | Percheron |
| 2,651,647 A | 9/1953 | Greenfield |
| 2,656,308 A | 10/1953 | Pettyjohn |
| 3,041,174 A | 6/1962 | Ehlert |
| 3,071,468 A | 1/1963 | Docken |
| 3,170,794 A | 2/1965 | Jeffreys et al. |
| 3,249,442 A | 5/1966 | Keyes et al. |
| 3,498,793 A | 3/1970 | Page et al. |
| 3,547,652 A | 12/1970 | Jeffreys |
| 3,561,973 A | 2/1971 | Rutman |
| 3,659,638 A | 5/1972 | Paoli |
| 3,674,640 A | 7/1972 | Takeda et al. |
| 3,692,538 A | 9/1972 | Moss et al. |
| 3,796,811 A | 3/1974 | Huth et al. |

(Continued)

FOREIGN PATENT DOCUMENTS

| | | |
|---|---|---|
| AU | 45032/72 | 1/1974 |
| CA | 890866 | 1/1972 |
| EP | 0348506 | 1/1990 |
| SU | 441915 | 12/1974 |

OTHER PUBLICATIONS

Calkins et al. Adding enzymes to improve beef tenderness (2007) www.beefresearch.org, accessed Jun. 5, 2013.*

(Continued)

*Primary Examiner* — Humera Sheikh
*Assistant Examiner* — Subbalakshmi Prakash
(74) *Attorney, Agent, or Firm* — Klarquist Sparkman, LLP

(57) ABSTRACT

Methods and apparatus for producing a particulate proteinaceous product are disclosed. Raw animal matter comminuted. Hydrolysing enzymes are added to preheated food-grade oil and added to the ground matter. The resulting suspension is preheated to hydrolysis temperature. Controlled hydrolysis of proteins in the suspension achieves a predetermined partial hydrolysis of the proteins to form a hydrolysate/oil suspension. At the desired level of hydrolysis the enzymes are heat-inactivated. Non-digestible solids are removed from the suspension and the suspension is pasteurized and partially dehydrated to concentrate the hydrolysate. Some of the oil is removed to form the product. The method and apparatus exhibit substantial resistance to equipment clogging.

22 Claims, 5 Drawing Sheets

(56) References Cited

U.S. PATENT DOCUMENTS

| | | | |
|---|---|---|---|
| 3,861,293 A | 1/1975 | Buffa et al. | |
| 3,928,630 A | 12/1975 | Perini | |
| 3,970,520 A | 7/1976 | Feldman et al. | |
| 4,176,199 A | 11/1979 | Vollmer et al. | |
| 4,185,121 A | 1/1980 | Huster et al. | |
| 4,237,003 A | 12/1980 | El-Sayed | |
| 4,293,571 A | 10/1981 | Olofsson et al. | |
| 4,293,583 A | 10/1981 | Farr et al. | |
| 4,361,586 A | 11/1982 | Meinke | |
| 4,389,423 A | 6/1983 | Madsen | |
| 4,405,649 A | 9/1983 | Jeffreys et al. | |
| 4,443,540 A | 4/1984 | Chervan et al. | |
| 4,526,791 A | 7/1985 | Young | |
| 4,542,686 A | 9/1985 | Bansal | |
| 4,708,055 A | 11/1987 | Matsumoto et al. | |
| 4,725,443 A * | 2/1988 | Narushima et al. | 426/56 |
| 4,846,054 A | 7/1989 | Mange et al. | |
| 4,863,746 A | 9/1989 | Uchida et al. | |
| 4,901,635 A | 2/1990 | Williams | |
| 4,976,973 A | 12/1990 | Shirakawa et al. | |
| 5,053,234 A * | 10/1991 | Anderson et al. | 426/59 |
| 5,113,755 A | 5/1992 | Anderson et al. | |
| 5,162,129 A | 11/1992 | Anderson et al. | |
| 5,356,647 A | 10/1994 | Mason et al. | |
| 5,607,840 A | 3/1997 | Van Gorp et al. | |
| 5,985,337 A | 11/1999 | Blortz et al. | |
| 6,056,981 A | 5/2000 | Saxby | |
| 6,372,282 B1 | 4/2002 | Edens et al. | |
| 6,803,062 B2 | 10/2004 | Oyama et al. | |
| 7,070,953 B1 | 7/2006 | Bjarnason et al. | |

OTHER PUBLICATIONS

Lee et al., "Process Requirements and Properties of Spray-Dried Squid Protein," *J. Food Sci.* 39:735-738 (1974).

Masters, "Spray Drying, The Unit Operation Today," *Indus. & Eng. Chem.* 60:53-63 (1968).

Masters et al., "Spray Drying Techniques for By-Product Recovery," *Process Biochem.*, 13 (1978).

*McGraw-Hill Encyclopedia of Science and Technology*, p. 575 (1982).

Robe, "Tomato Paste in Powder Form," *Food Processing* (1968).

\* cited by examiner

METHODS AND APPARATUS FOR PRODUCING PARTIALLY HYDROLYSED PROTEINACEOUS PRODUCTS

CROSS-REFERENCE TO RELATED APPLICATION

This application claims priority to, and the benefit of, U.S. Provisional Application No. 61/120,027, filed on Dec. 4, 2008, which is incorporated herein by reference in its entirety.

FIELD

This disclosure pertains to, inter alia, methods and apparatus for producing proteinaceous products from partial hydrolysis of raw animal matter.

BACKGROUND

Proteins are basic building blocks of life. To man, mammals, fowl, fish, and reptiles, proteins are an essential component of a healthy diet. Protein deterioration and putrefaction from spoilage limits the effective and efficient use of available resources. For example, raw animal protein generally putrefies and spoils within hours when left at room temperature. Through the years, methods such as salting, drying, canning, refrigeration, modified atmosphere packaging, and food irradiation have been developed to preserve or enhance the shelf-life of animal proteins.

Even with these advances in protein preservation mentioned, the need as well as the goal to improve methods and techniques to preserve protein while maintaining a protein's functional and nutritional qualities, continues in the academic and business world. And with an ever-increasing world population requiring more and more protein, innovation and invention in this field is increasingly important economically and environmentally.

Numerous attempts and extensive research for more than 60 years has gone into the development of a commercially acceptable method for enzymatically hydrolysing proteinaceous raw material such as meat, fowl, fish, and their by-products. For example, U.S. Pat. Nos. 7,070,953 to Bjarnason et al.; 6,803,062 to Yamamoto et al.; 6,372,282 to Edens et al.; 6,056,981 to Saxby; 5,985,337 to Blortz et al.; 5,607,840, to Van Gorp et al.; 5,356,647 to Loosen et al.; 5,053,234 to Anderson et al.; 4,976,973 to Shirakawa et al.; 4,863,746 to Uchida et al.; 4,361,586 to Meinke; 4,293,571 to Olofsson et al.; 4,176,199 to Vollmer et al.; 3,970,520 to Feldman et al.; 3,928,630 to Perini; 3,796,811 to Huth et al.; 3,561,973 to Rutman; 3,249,442 to Keyes et al.; 3,071,468 to Docken; 2,651,647 to Greenfield; 2,350,811 to Percheron; and Russian Patent No. 441,915 all disclose methods (with the exception of 2,651,647 to Greenfield) by which animal proteins are enzymatically hydrolysed to produce digested protein products. However, the methods disclosed in these patents have particular disadvantages and none are ideal. For example, the methods of U.S. Pat. Nos. 5,356,637, 5,607,840, 5,985,337, 6,056,981, and 6,803,062 require digestion times exceeding 4 hours. While the method of U.S. Pat. No. 6,056,981 uses no external enzymes, relying on autolysis, and the method of U.S. Pat. No. 7,070,953 relies primarily on cod proteases, in both cases the scope and utility value of the resulting methods are restricted relative to the present invention.

The present invention addresses, inter alia, certain improvements to methods and apparatus disclosed in U.S. Pat. Nos. 5,053,234 and 5,133,755 to Anderson et al., both incorporated herein by reference in their respective entireties. Specifically, the improvements disclosed herein provide methods and apparatus that can be used to produce partially hydrolysed particulate proteinaceous product under conditions of reduced process interruptions. The instant methods and apparatus provide greater fluidity and lubricity of the raw material as it is being processed to reduce clogging and to improve process efficiency. The instant methods and apparatus also provide improved efficiency of heat transfer into the raw material to reduce energy costs. The instant methods and apparatus also provide increased efficiency of proteolytic reactions performed on the raw material. The instant methods and apparatus produce a hydrolysed proteinaceous product that is free of steam contaminants. The instant methods and apparatus also provide improved control of the level of oil in the partially hydrolysed proteinaceous product.

SUMMARY

Disclosed herein are, inter alia, improved methods and apparatus for preparing a substantially non-denatured, partially hydrolysed proteinaceous product from raw animal matter. An embodiment of the subject methods comprises providing the raw animal in a ground condition and adding preheated food grade oil to form an animal matter/oil suspension. The proteins in the animal matter/oil suspension are hydrolysed using proteolytic enzymes, where the hydrolysis is performed at a temperature within a range conducive for hydrolytic activity of the enzymes without denaturing the protein and for a time period sufficient to achieve a preselected degree of partial hydrolysis of the protein, to form a hydrolysate/oil suspension. The hydrolysate/oil suspension is then heated sufficiently to deactivate the proteolytic enzymes. At least some non-digestible solids are then removed from the hydrolysate/oil suspension. The hydrolysate/oil suspension also desirably is pasteurized. The concentration of water in the suspension is reduced, e.g., by evaporation. Then, a portion of the oil is removed from the suspension to form a particulate, partially hydrolysed, non-denatured proteinaceous product.

The foregoing embodiment can be regarded as including the following three basic stages: predigestion heating of a mixture of raw animal material, food-grade oil, and enzymes; partial digestion (hydrolysis) of the protein in the material; and removal of excess moisture from the hydrolysate to form the product. The heating and hydrolysis steps can be performed using one or more heat exchangers having no moving parts and that achieve plug flow of the material through the heat exchangers.

Upon reaching a desired state of hydrolysis, further hydrolysis is stopped, e.g., by application of heat, while avoiding a temperature that would significantly denature the hydrolysate.

Removing non-digestible solids can be achieved by passage of the hydrolysate/oil suspension through a mechanical separator. Water removal can be performed by passing the hydrolysate/oil suspension at a controlled flow-rate through one or more evaporators. Oil-removal from the hydrolysate/oil suspension can be performed by using a centrifuge or analogous device. At least a portion of the removed oil can be used as the food-grade oil added to the comminuted animal matter in the prehydrolysis heating stage.

The foregoing and additional features and advantages of the invention will be more readily apparent from the following detailed description, which proceeds with reference to the accompanying drawings.

DETAILED DESCRIPTION

Figure 1:
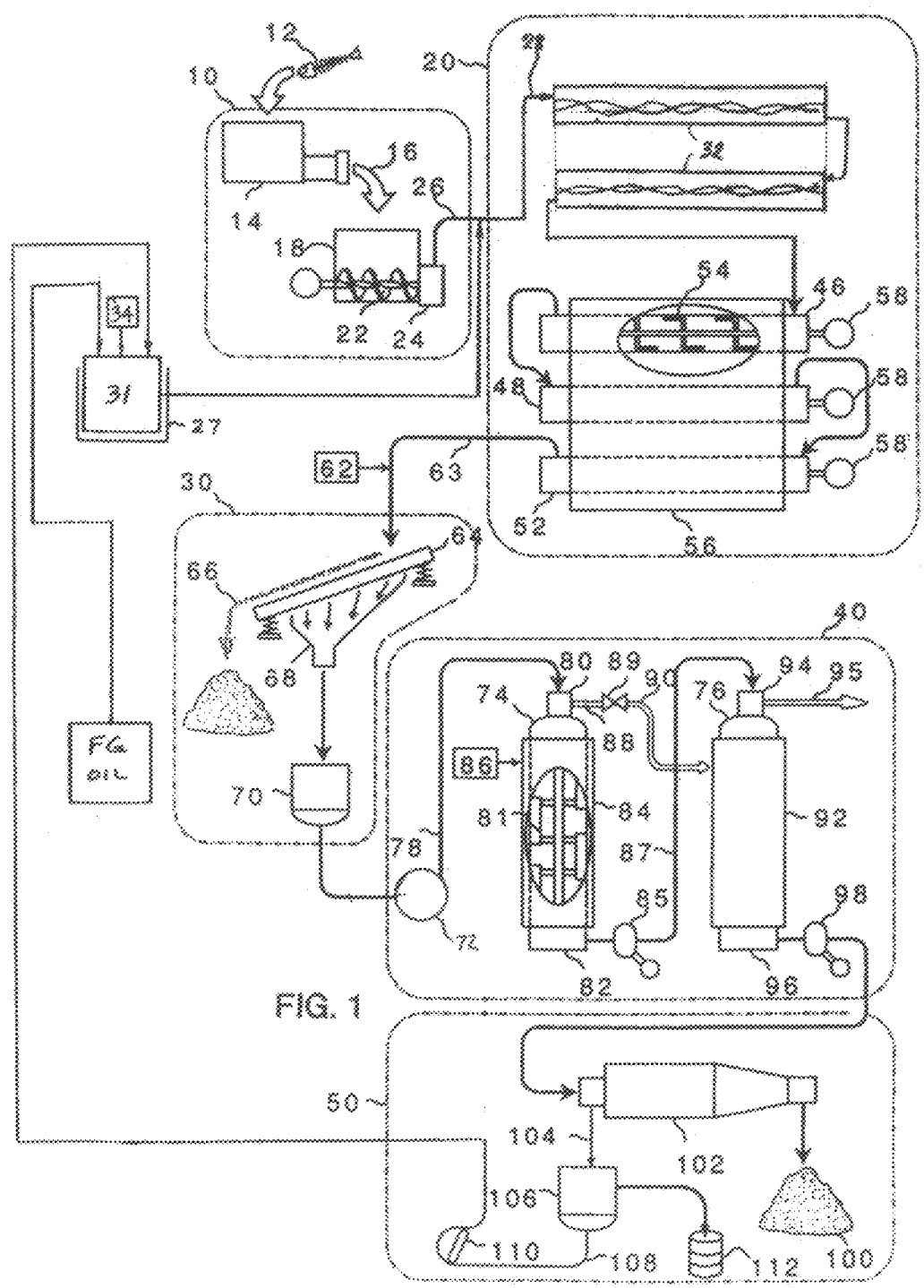
FIG. 1 is a schematic flow diagram of an embodiment of the apparatus and method.

An embodiment of the subject apparatus and process is shown schematically in FIG. 1. The process comprises multiple stages, each of which comprising one or more discrete steps. The stages are, in order of occurrence, a mulling stage 10, a protein-hydrolysis stage 20, a separation stage 30, a concentration stage 40, and an oil-separation stage 50. These five stages collectively convert raw animal matter 12 into a particulate, partially hydrolysed, non-denatured proteinaceous product 100. As used herein, "raw animal matter" denotes any of various items from a group comprising abattoir remains, other residual animal matter, fillet frames, trash fish, spawned-out fish, whole fish, skates, rays, shark, poultry, mutton, beef, pork, shrimp, krill, squid, crab, oysters, clams, locust, animal by-products, usable entrails, and the like.

Typically, the product 100 has a somewhat dry, powdery or flaky consistency. It is readily compressible into pellets, cakes, or blocks if desired (not shown). For example, one desired form is pellets having a diameter of about ⅛ to ¼ inch. Such pellets are easy to convey via, for example, pneumatic systems. The product 100 may also be pressed into cake or block forms (not shown), each typically weighing about 10 kg, which is also easy to transport. Cakes and blocks advantageously reduce the surface area of the product available for oxidation. Although the product 100 is dry to the touch, it has a relatively high concentration of oil. The oil not only facilitates compressing the product into pellets or blocks but also confers other benefits. First, since the product 100 is intended to be used as a food, food supplement, or nutraceutical, the oil tends to make the product more flavorful when presented for consumption. For example, if the product 100 derived from krill is used in the manufacture of companion pet food, the oil enhances its odor and taste appeal. Second, the oil is "high quality" which means that it is readily digestible and nutritious. For example, a relatively high oil content in fish feed readily fulfills the energy requirements of the fish, thus enabling the protein in the feed to be used predominantly for growth rather than catabolism.

Referring further to FIG. 1, raw animal matter 12 passes through the mulling stage 10, in which the raw animal matter 12 is reduced, if necessary, to a ground condition. Hence, the mulling stage is optional. If the raw animal matter is inherently comminuted (e.g., krill), then the mulling stage may not be necessary. Mulling is generally performed by passing the raw animal matter through a grinder 14 or analogous device. As suggested in FIG. 1, the grinder 14 reduces not only the proteinaceous component of the animal matter 12 to a ground condition, but also comminutes any bones, scales, shell, and other parts associated therewith. As used herein, a "ground condition" is a particulate form, wherein the particles have a median diameter within a range of about 1/16 inch to ½ inch. Preferably, the particles have a median diameter of about ¼ inch. In many instances, the ground animal matter has the appearance of ground meat used for human food.

After grinding, the ground animal matter is passed 16 into a transfer bin 18. The transfer bin 18 is desirable because it serves to even out the flow of material exiting the grinder 14, since grinders and analogous mulling devices typically do not process material with a constant-flow throughput. Ground animal matter contained in the transfer bin 18 gravitates toward a rotating auger 22 or analogous mass-conveying device that urges flow of the ground animal matter toward a first positive-displacement pump 24. The pump 24 desirably exhibits positive-displacement and constant-flow delivery.

Whereas the animal matter can sometimes be digested using endogenous proteolytic enzymes, it is usually desirable to add extraneous proteolytic enzymes 34 to the ground animal matter. Adding extraneous enzymes 34 ensures consistency of the overall process and product 100. The enzymes 34 desirably are of a type generally known as proteolytic or peptide-hydrolysing enzymes, such as papain, keratinase, and the like. Proteolytic enzymes cleave the large protein molecules of the ground animal matter into smaller molecules by hydrolysing peptide bonds along the protein backbone. The comminuted animal matter desirably receives the enzymes before the suspension enters the heat exchanger 32. As the suspension passes through the heat exchanger 32 a mixing action is imparted to the suspension, which aids the dispersal of the enzymes throughout the suspension.

The extraneous enzymes 34 can be a commercially available preparation such as "Coralase L 10" produced by Rohm GmbH, Postfach 4242, Kirschenalle, D-6100, Darmstadt, Germany. In the case of fish, the amount of this preparation required is about 300 to 400 mL per 1000 pounds of raw fish matter. More enzyme may be required when processing matter from terrestrial animals such as bovine matter.

The extraneous enzymes 34 are premixed with a predetermined amount of food-grade oil (e.g., about 40 to 60 pounds food-grade oil per 1000 pounds of raw fish matter) before adding the resulting enzyme suspension to the ground animal matter. Desirably, the oil is at a temperature within a range of about 135° F. to about 170° F., more preferably between 140° F. and 155° F., and even more preferably between 145° F. and 150° F. (the optimum digestion temperature of papain) before the enzymes are added.

To such end, the oil is preheated. In some embodiments preheating of the oil is performed using a heating device 27 (e.g., manufactured by Pick Heaters, Inc, West Bend, Wis.) situated in a temperature-controlled tank 31 holding the mixture. Dispensing of the mixture from the tank can be achieved using a pump (not shown) having a suitable flow-rate. The addition of the preheated oil-enzyme mixture to the suspension of ground animal matter converts the suspension into an oil/enzyme/ground matter suspension. This addition of the preheated oil-enzyme mixture at this stage represents a novel departure from methods disclosed in U.S. Pat. Nos. 5,053,234 and 5,113,755. The added oil at this stage provides fluidity, lubricity, and improved heat transfer through direct product contact. The fact that the oil is prewarmed also allows enzymatic digestion to immediately commence at a favorable temperature. The added oil also allows most of the water to be removed later without the need to add more oil before the suspension enters the evaporators 74, 76 later downstream. Thus, the suspension can pass through the evaporators without becoming a stiff, unpumpable paste that otherwise would clog the evaporators.

In an alternative embodiment preheating of the oil can be performed using a heater and direct steam injection. This alternative embodiment is less desirable because the water added by the steam must be removed later by evaporation. Also, food-grade steam adds extra expense, and the enzymes would need to be introduced downstream of the heater but before the inlet 28.

The amount of water in the suspension of ground animal matter at this stage of the process is generally dictated by the naturally occurring amount of water present in the raw animal matter 12. With fish, for example, the natural water content is about 75%. Usually, it is not necessary to add additional water to the suspension. Increasing fluidity by adding water is usually unnecessary because of the added oil.

Aside from extraneous enzymes 34 and oil, it is usually unnecessary at this stage to add any other ingredients to the ground animal matter. For example, no extraneous buffering or pH-adjusting ingredients are necessary. The natural pH of the suspension is sufficient, generally within the range of 6 to 6.5.

The first pump 24 urges flow of the ground animal matter through a conduit 26 to the inlet 28 of a heat exchanger 32. An accurate hydraulic flow-rate through the heat exchanger 32 is achieved by presetting and accurately controlling the pumping rate of the first pump 24. The heat-exchanger desirably is a shell-and-tube type, for example a HIPEX "Mixchanger" (see http://www.hipex.com.au/mixchanger.htm). This type of evaporator includes a fluted jacket, a central stationary mixing element, but no moving parts. See FIGS. 2 and 3. The central mixing element has an auger configuration. A hot heat-exchange medium (e.g., hot water) is circulated through the central mixing element and the jacket is also heated. Meanwhile, the first pump 24 urges flow of the animal matter/oil/enzyme suspension longitudinally through the jacket. During such flow, the suspension is forced along the path dictated by the central mixing element and thus interacts with the central mixing element and flutes of the jacket. Heating of the suspension is the result of the heated oil added beforehand, as well as interaction of the suspension with the shell and central mixing element. The suspension experiences even heating and plug flow during its passage through the heat exchanger.

To facilitate desired proteolytic action, the heat exchanger 32 warms the oil/enzyme/ground matter suspension to a temperature generally within a range of about 140° F. to 150° F. A temperature of about 140° F. is usually optimal for endogenous proteolytic enzymes, whereas a temperature of about 150° F. is usually optimal for extraneous enzymes such as papain. Hence, if one wishes to suppress action of endogenous enzymes when extraneous enzymes 34 are added, the suspension should be at about 150° F. A temperature in excess of 150° F. is disadvantageous because exceeding 150° F. causes protein denaturation and enzyme deactivation. A temperature lower than about 140° F., while not necessarily disadvantageous, will usually require a longer time to achieve a desired degree of protein hydrolysis during the subsequent enzymatic hydrolysis step (described below).

As noted above, the jacket and central mixing element of the heat exchanger 32 are heated. The jacket can be heated by circulating a hot fluid heat-exchange medium in a space between the jacket and an outer shell. Similarly, the heat-exchange medium can be passed through the mixing element. Other heating techniques are also possible.

Since the first pump 24 propels the ground suspension of animal matter at a preset constant hydraulic flow-rate, the transit time of the ground suspension through the heat exchanger 32 is accurately known. This ensures reliable and consistent attainment of the desired hydrolysis temperature of the oil/enzyme/ground matter suspension.

Material ("pre-digestion mixture") warmed by the heat exchanger passes to the protein-hydrolysis stage 20. In the protein-hydrolysis stage the proteins in the suspension are enzymatically hydrolysed at a temperature conducive for such hydrolysis without significantly denaturing the protein in the suspension. Hydrolysis is allowed to proceed to a predetermined extent, but not to total hydrolysis. The product of this hydrolysis is a liquid hydrolysate.

In the embodiment shown in FIG. 1, one or more digesters separate from the heat-exchanger 32 are used for performing hydrolysis. Depicted in FIG. 1 are three digesters 46, 48, 52 connected together in series. It will be understood that as few as one digester could be used, or multiple digesters. A series of smaller digesters, as shown in FIG. 1, can provide tighter control over the degree of hydrolysis and reduce the possibility of non-digestible solids settling out.

Small elongated digesters, such as those 46, 48, 52 shown in FIG. 1, are also advantageous in that they greatly facilitate a desirable "plug flow" passage of material through the digesters. "Plug flow" denotes flow behavior in which each quantum of suspension flows over the same path length through the digester. Plug flow ensures that each quantum of suspension passes through the digester in substantially the same amount of time, thereby preventing over-digestion or under-digestion of any portion of the suspension. In this way, the number-average molecular weight of the partially hydrolysed protein molecules comprising the product 100 can be tightly controlled to a predetermined value, thereby ensuring maximal nutritive value and resistance to oxidation of the product 100. Plug flow also permits more rapid digestion than with prior-art methods.

A general target value for the number-average molecular weight is within a range of about 15,000 to about 30,000 Daltons, but other values can be selected and reliably achieved, depending upon the intended use of the product 100. A key benefit of carefully controlling the degree of protein hydrolysis is that minimal changes are imparted to amino acids comprising the animal protein in the product 100, thereby maximizing nutritive value of the product 100.

The number of digesters can vary, depending upon a number of factors, including the source of the animal matter, the water content, the desired volume throughput, the digestion temperature, the type and concentration of enzymes, the capacity of each individual digester, and the degree of digestion desired. Use of multiple digesters can achieve faster digestion to the desired degree of hydrolysis than a single larger digester exhibiting the same transit time as the collective transit times of the smaller digesters. In FIG. 1, each digester 46, 48, 52 has a volumetric capacity configured such that a quantum of suspension passes through a digester in about 20 to 40 minutes' transit time.

Referring further to FIG. 1, each digester 46, 48, 52 desirably includes plural rotatable paddles 54 or analogous mixing devices to prevent channeling of the digestion mixture as it passes through the digester. The paddles are configured and rotated to provide plug flow while preventing over-mixing. Alternatively, the digesters can have a configuration similar to the hybrid shell-and-tube heat exchanger, so as to eliminate moving parts. The paddles 54 desirably also prevent non-digestible solids such as bone particles from settling along the bottom of each digester, which may lead to clogging.

The digesters can be insulated, either collectively as shown in FIG. 1 or individually, to maintain optimal temperature for enzymatic digestion as the suspension passes through the digesters. The temperature inside each digester can be measured and displayed by thermometers 58 or analogous devices.

Figure 3:
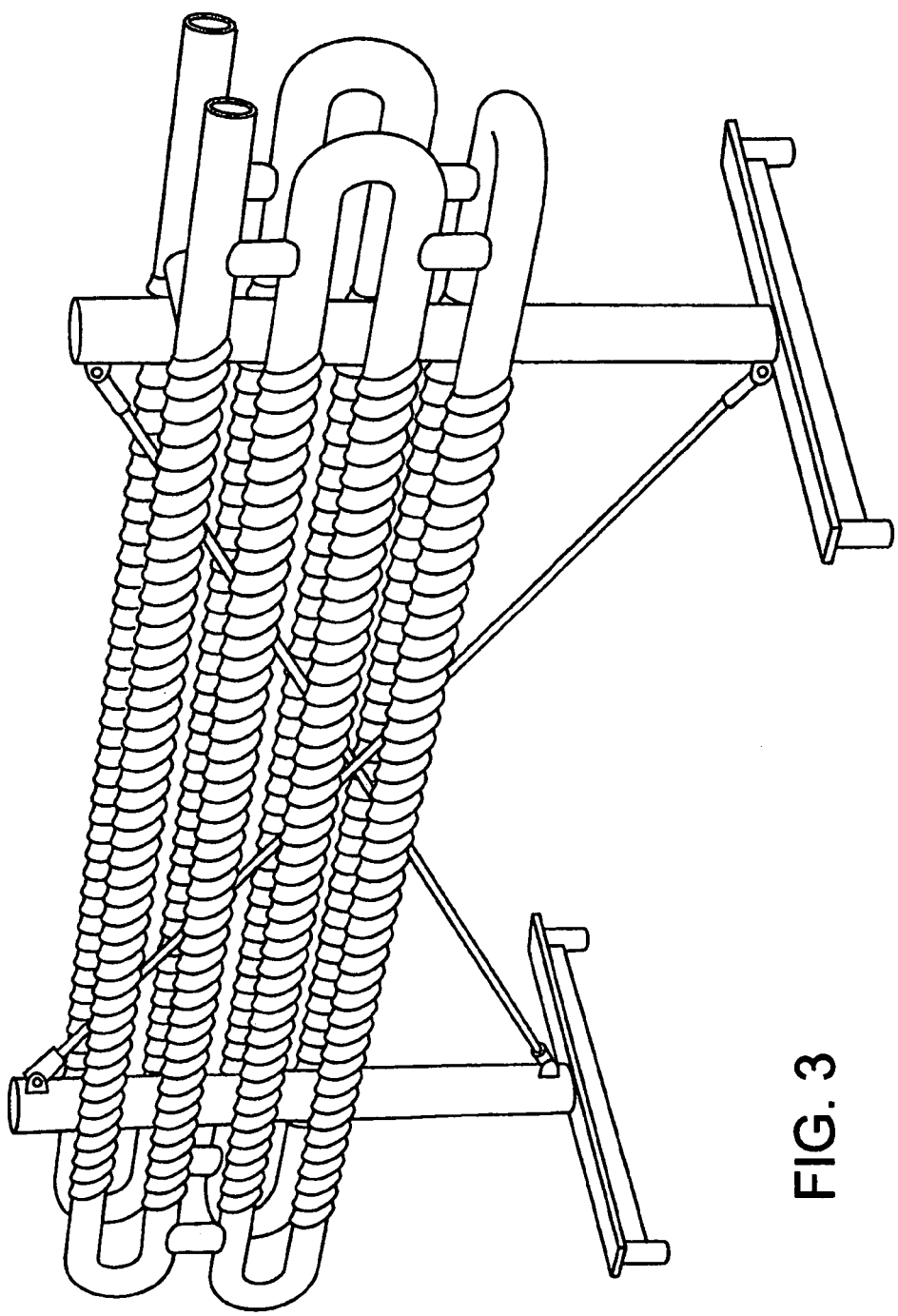
FIG. 3 shows a series (twelve) of heat-exchangers of an advantageous type.
Figure 4:
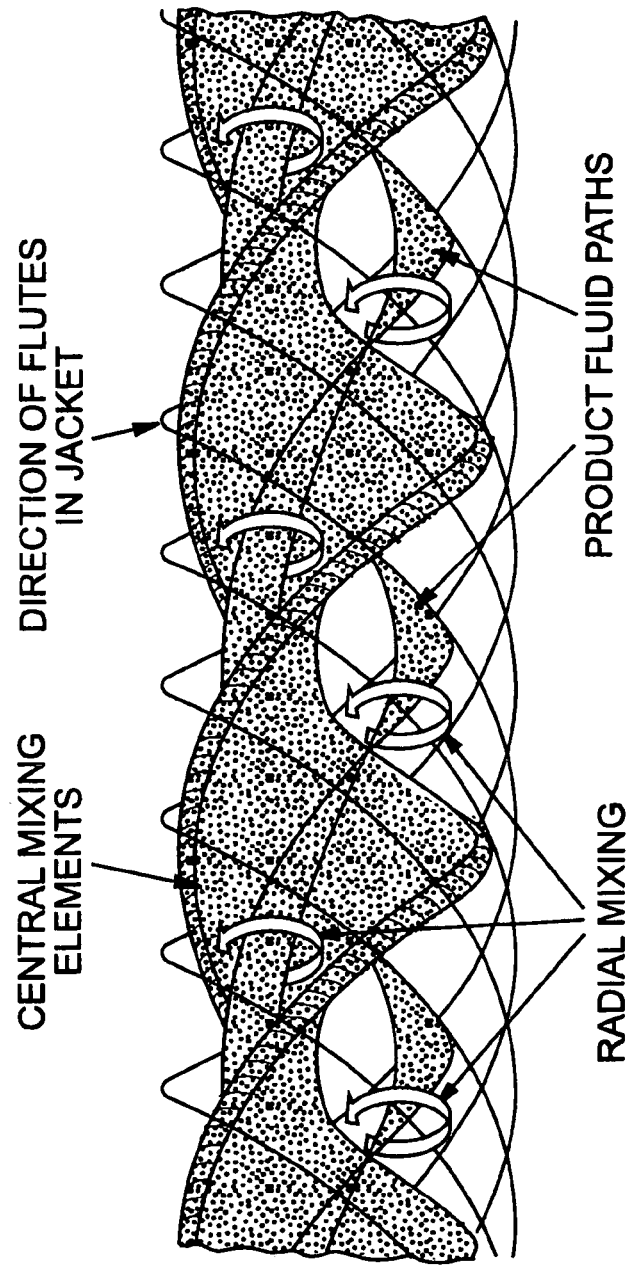
FIG. 4 depicts flow of suspension through a portion of a heat-exchanger shown in FIG. 3.

In an alternative embodiment of the FIG.-1 configuration, the heat-exchange function is combined with the digester function. In other words, the heat exchanger is configured in such a way that it performs both pre-digestion heating and digestion. A particularly advantageous manner of performing both functions simultaneously is to employ one or more heat-exchanger units through which the suspension is transported in a plug-flow manner and in a manner ensuring thorough mixing and temperature control. Referring to FIG. 1, this alternative embodiment essentially eliminates the digesters 46 48, 52 by combining their function with the heat exchangers 32. To such end, multiple heat-exchanger units, such as the Hipex Mixchanger (Thomastown, Australia), are simply connected in series and/or parallel, as required, with each other to form a heat-exchanger arrangement. (See, for example, the arrangement shown in FIG. 3, in which twelve heat-exchanger units are arranged in series. It will be understood that the number of heat-exchanger units actually used is not limited to twelve but rather can range from one to two or more.) The suspension of oil, enzymes, and ground matter enters one end, and partially hydrolysed protein exits the other end. Each heat-exchanger unit in FIG. 3 includes a longitudinally extended fluted jacket and an internal central mixing element (see FIG. 4) extending longitudinally in the lumen of the jacket. The jacket of one or more of the heat-exchanger units can be jacketed and/or insulated to achieve desired temperature control. In FIG. 4, note the helical direction of the jacket flutes and of the central mixing element. As the suspension passes through this heat-exchanger unit, it flows in a helical manner as guided by the central mixing element. This passage is also influenced by the jacket flutes, which superimpose a radial mixing action on the suspension as the suspension passes through the heat-exchanger unit. As a result, the suspension experiences thorough mixing as it travels in a plug-flow manner through each heat-exchanger unit. Advantages of such an arrangement include: elimination of moving parts, high efficiency, more rapid hydrolysis, improved temperature control through pre-heat and hydrolysis, better control of the degree of hydrolysis, and uninterrupted continuation of plug flow from preheat through hydrolysis. An additional benefit is the possible elimination, downstream, of a need to inject live steam into the hydrolysate to pasteurize and deactivate the proteolytic enzymes prior to bone separation (see discussion below of steam injection).

Digestion transforms the pre-digestion mixture into a suspension of partially hydrolysed protein and oil. The suspension is markedly fluid, liquid-like. A key benefit of the partial hydrolysis of the present method is that the resulting suspension is no longer subject to denaturation. This is important because downstream process steps are performed at higher temperatures that would denature non-hydrolysed proteins.

The partially hydrolyzed suspension still contains active enzymes. It is desirable in many instances to deactivate the enzymes as the suspension exits through the digesters or immediately afterward. Application of heat is a preferred way to deactivate the enzymes. Heat may be applied by, for example, controllably injecting steam directly into the suspension. For example, in FIG. 1 live steam from a steam source 62 is injected into a conduit 63 conducting the aqueous suspension away from the last digester 52. An alternative to injecting steam is passing the aqueous suspension through another heat exchanger (not shown) for further heating. Other heating devices apparatus known in the art may alternatively be used. As noted above, selection of an appropriate heat exchanger may allow elimination of this step.

A general temperature range for heat-deactivating the enzymes in the aqueous suspension is about 175° F. to about 200° F. These temperatures also advantageously reduce the viscosity of the suspension. At the lower digestion temperature, the suspension may comprise solid fatty material that could form clogs at the material-separation stage 30 located downstream. Elevating the temperature of the suspension to about 175° F. to 200° F., sufficient for enzyme deactivation, tends to soften, break up, and/or liquefy fatty solids, which decreases the probability of their forming clogs. The actual temperature for optimal results may depend upon the source of the proteinaceous material. For example, a temperature of 190° F. to 200° F. is generally optimal for poultry, whereas a temperature of 175° F. to 185° F. is generally optimal for fish.

In the material-separation stage 30, the heated aqueous suspension can be passed through an inclined vibrating screen 64 or other suitable separation device that separates non-digestible solids 66 (e.g., bones, scales, shells) from the liquid 68 as the liquid passes through the screen 64. Typically, the screen size is between 40 and 60 meshes per inch. The vibration and inclined orientation of the screen 64 facilitate liquid passage therethrough while keeping the screen free of non-digested solids 66 that do not pass through. The captured non-digested solids can be collected, dried, and further processed into bone meal and similar products (not shown).

If necessary, a spray (not shown) of hot water (175° F. to 200° F.) can be directed at the screen to recover hydrolysed protein that would otherwise adhere to the non-digestible solids. This results in a higher product recovery and "cleaner" non-digestible solids but adds additional water to the suspension which will have to be removed later in the concentration stage 40.

As an alternative to the vibrating screen 64, other analogous material-separation devices may be employed for removing the non-digestible solids 66. For example, a basket centrifuge, a Brown finisher/extractor, or vacuum screen may be used (not shown). The vibrating screen 64 has advantages such as lower cost and simpler construction compared to alternative devices such as a centrifuge.

In this embodiment it is usually unnecessary to recirculate hydrolysate back through the digesters. The combination of accurately controlled protein hydrolysis combined with post-digestion heating usually renders such recirculation unnecessary. Also, recirculation may increase protein hydrolysis which would negate the benefit achieved with carefully controlled digestion. An example instance in which recirculation may be indicated is the raw animal matter 12 comprising a very high proportion of non-digestible solids such as bone or shells, such as may be found in shrimp waste. However, even in these instances, a problem with excessive viscosity due to large amounts of bone or shells can usually be solved by merely supplying additional fluidity to the suspension. Recirculation is usually performed by removing a portion of the suspension downstream of the screen 64 for return to either the transfer bin 14 or just upstream of a digester 46.

The liquid 68 passing through the screen 64, namely the suspension of partially hydrolysed protein, is collected and desirably routed to a surge tank 70 that essentially serves as a holding vessel. The surge tank 70 is advantageous especially whenever the hydraulic flow-rate out of the digesters is uneven and the downstream concentration stage 40 requires a substantially constant hydraulic flow-rate.

In the concentration stage 40 the suspension of partially hydrolysed protein collected in the surge tank 70 is withdrawn from the surge tank 70 using a positive-displacement second pump 72 providing an accurate flow-rate.

The concentration stage 40 in one embodiment includes a first evaporator 74 and a second evaporator 76 coupled in series downstream of the second pump 72. The first evaporator 74 can be used to perform two tasks, namely pasteurizing the aqueous suspension and removing a substantial portion of the water from the suspension. The second evaporator 76 completes the desired degree of water removal. The evaporators are arranged relative to each other in what is known in the art as a "double-effect" configuration as shown in FIG. 1, wherein the vapor evolved from the first evaporator 74 is used as the heating medium in the subsequent second evaporator 76. Each evaporator 74, 76, in such a configuration is called an "effect." Other configurations such as "triple effect" and "recompression" can also be used, which may be even more energy efficient than "double effect." The number of "effects" employed depends upon the available overall temperature difference and upon the economics of the process, where additional "effects" result in capital cost increases which may offset the savings achieved in energy costs.

The evaporators 74, 76 are preferably of a "wiped-film" type. They are vertically oriented where the liquid to be concentrated, respectively, enters at the top and exits at the bottom. As an alternative to wiped-film evaporators, shell-and-tube evaporators may be used. Desirably, the evaporator(s) perform both water removal and pasteurization.

In an alternative embodiment, only one evaporator (not shown) is used. A single evaporator desirably is capable of performing both pasteurization and water removal. Alternatively, a single evaporator may be used solely for water removal and some other type of apparatus used for pasteurization upstream of the single evaporator. A single wiped-film evaporator is less desirable than multiple evaporators because the single evaporator requires more energy to remove the same amount of residual water than the two-evaporator configuration shown.

Figure 2:
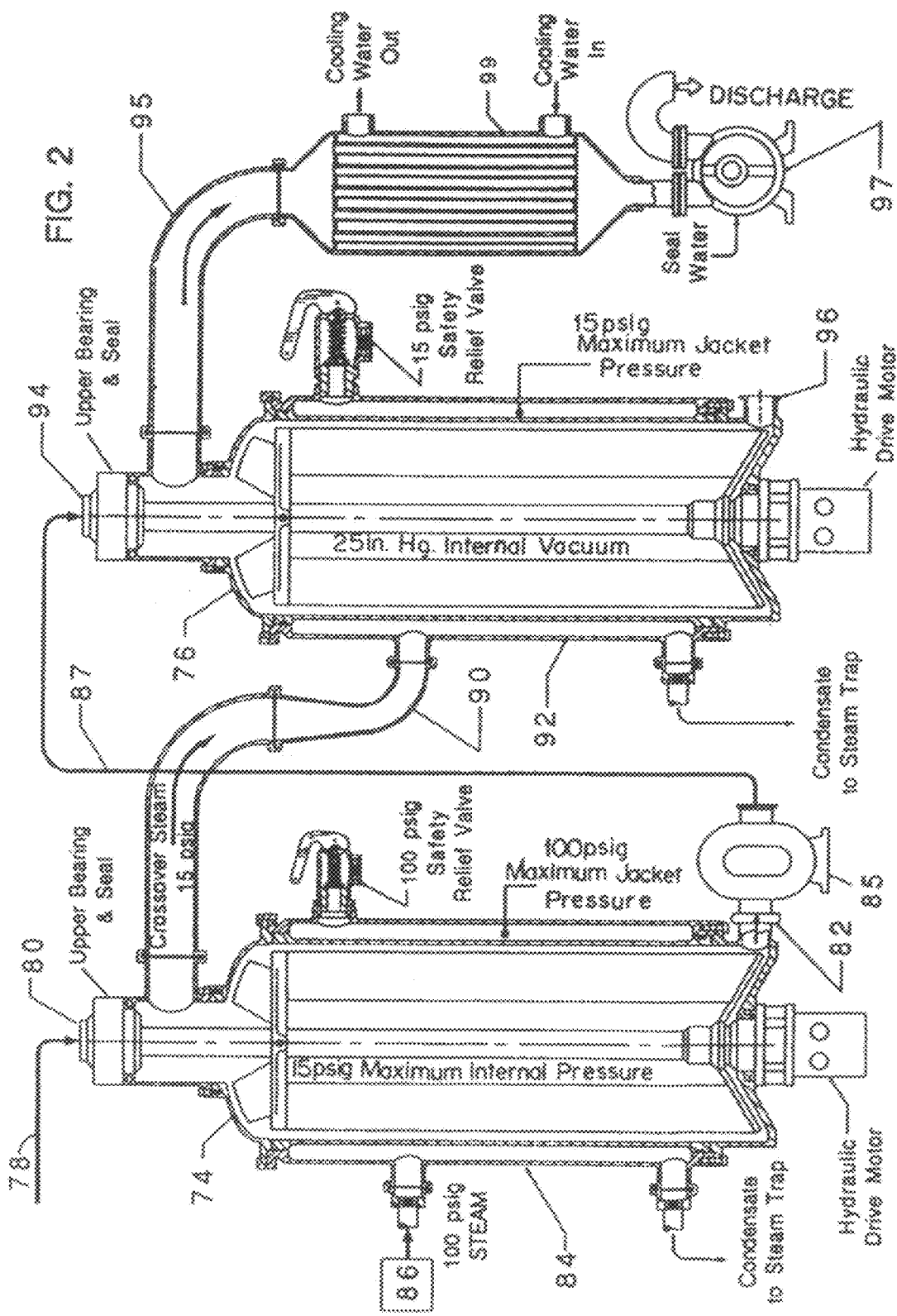
FIG. 2 is a close-up view of a portion of the FIG.-1 embodiment, showing sectional views of the first and second evaporators together with nearby equipment coupled thereto.

Referring further to FIG. 1, after passing through the second pump 72, the suspension of hydrolysate and oils is passed through a conduit 78 to a top end 80 of the first evaporator 74 (see also FIG. 2, showing details of the evaporator system shown schematically in FIG. 1). From the top end 80, the suspension passes downward through the first evaporator 74 to the bottom end 82 thereof. The first evaporator 74 is jacketed by an outer chamber 84 through which is passed a heating medium such as steam from an extraneous source 86. The outer chamber 84 surrounds an inner chamber (not shown) through which passes the protein-oil suspension from the top end 80 to the bottom end 82 of the first evaporator 74.

Passage of the hydrolysate-oil suspension through the first evaporator 74 desirably heats the suspension to a pasteurization temperature in the range of about 200° F. to about 250° F. at 0 to 15 psig pressure for about 10 to 20 seconds (transit time through the first evaporator 74). The transit time desirably is predetermined and dictated by the pumping rate of the second pump 72 and the volumetric capacity of the first evaporator 74. The pressure setting of a control valve 89 controls the temperature at which the suspension leaves the first evaporator 74 since the higher the pressure of the suspension, the higher the temperature at which the protein-oil suspension will boil. As the hydrolysate-oil suspension passes through the first evaporator 74 and becomes pasteurized, the heating imparted to the suspension therein also causes a substantial portion of the water to be removed from the suspension.

The inner chamber of the first evaporator 74 desirably includes an array of scraping or wiping blades 81 rotatable about the vertical longitudinal axis of the first evaporator 74. Alternatively, an analogous device for mixing of the suspension passing through the first evaporator 74 may be used. In the depicted configuration the array of blades 81 is rotated as the suspension passes through the first evaporator 74. The resulting mixing action increases heat transfer efficiency and prevents localized overheating of the suspension. The resulting increased thermal transfer efficiency allows use of a smaller and less costly evaporator.

After leaving the first evaporator 74 through the bottom end 78 thereof, the pasteurized hydrolysate-oil suspension passes through an evaporator transfer pump 85 (e.g., a positive-displacement rotary pump). So long as the evaporator transfer pump 85 pumps at a higher volumetric rate than the second pump 72 the first evaporator 74 does not fill up. This continuous unloading of the first evaporator 74 prevents a long residence time of the hydrolysate-oil suspension passing therethrough.

Vapor from the first evaporator 74 is conducted through a conduit 88, through the control valve 89, and through a conduit 90 to an outer jacket 92 of the second evaporator 76. This provides an energy-efficient process in which maximal heat is recovered from the steam. The control valve 89 (not shown in FIG. 2) is not required. But, this valve is preferred especially if the second evaporator 76 is sufficiently large to utilize all the vapor produced by the first evaporator 74.

Continuing further with FIGS. 1 and 2, the pasteurized hydrolysate-oil suspension, after passing through the evaporator transfer pump 85, is conducted through a conduit 87 to a first end 94 of the second evaporator 76. As the pasteurized suspension enters the second evaporator 76, the suspension encounters a sub-atmospheric pressure of about 15 to 25 inHg, which quickly lowers the temperature of the suspension to within a range of about 150° F. to about 160° F. The sub-atmospheric pressure is generated using a vacuum pump or analogous device (item 97 in FIG. 2) coupled to a conduit 95, preferably employing a condenser (item 99 in FIG. 2) coupled between the vacuum pump 97 and the second evaporator 74. The condenser 99 condenses the water vapor leaving the second evaporator 76 and thus reduces the size of vacuum pump required. The condenser 99 also precipitates many of the odoriferous compounds released by evaporation, thereby preventing their release into the atmosphere.

As the hydrolysate-oil suspension passes through the second evaporator 76, the suspension undergoes mild reheating to an exit temperature of about 175° F. to 200° F. as more water is removed therefrom. The suspension exits the second evaporator 76 at the latter temperature through a bottom end 96 thereof and evaporator discharge pump 98 coupled to the bottom end 96. The exit temperature is related to the moisture level of the protein-oil suspension. The less moisture left in the suspension, the higher the exit temperature. Monitoring the exit temperature while monitoring of the temperature of the water vapor exiting the second evaporator through a conduit 95 gives an indication of the amount of reheating of the suspension taking place in the second evaporator 76. Thus, such temperatures serve as an indication of the amount of residual moisture remaining in the protein-oil suspension. Temperature rises of 10° F. to 30° F. in the second evaporator 76 will result in final product moisture levels of 10 to 15 percent.

Since extraneous air is excluded from the hydrolysate-oil suspension as it passes through the evaporators 74 and 76, the possibility of oil oxidation is greatly reduced. As a result, the formation of odor-causing compounds is also reduced.

Another parameter affecting the temperature of hydrolysate-oil suspensions after passing through the second evaporator 76 is the level of sub-atmospheric pressure applied thereto. The lower the pressure, the greater the temperature drop of the suspension upon entering the second evaporator 76 and, consequently, the lower the temperature upon leaving the second evaporator 76.

The temperature at which moisture is evaporated from the suspension as it passes through the second evaporator 76 is important when processing suspensions derived from certain animal sources. For example, waste from Tilapia genera of fish as well as species such as black cod can produce suspensions that become unacceptably gummy when heated too high.

As can be seen, controlling the several parameters affecting temperature rise of the suspension passing through the second evaporator 76 directly affects the consistency and degree of water loss from the suspension.

Figure 5:
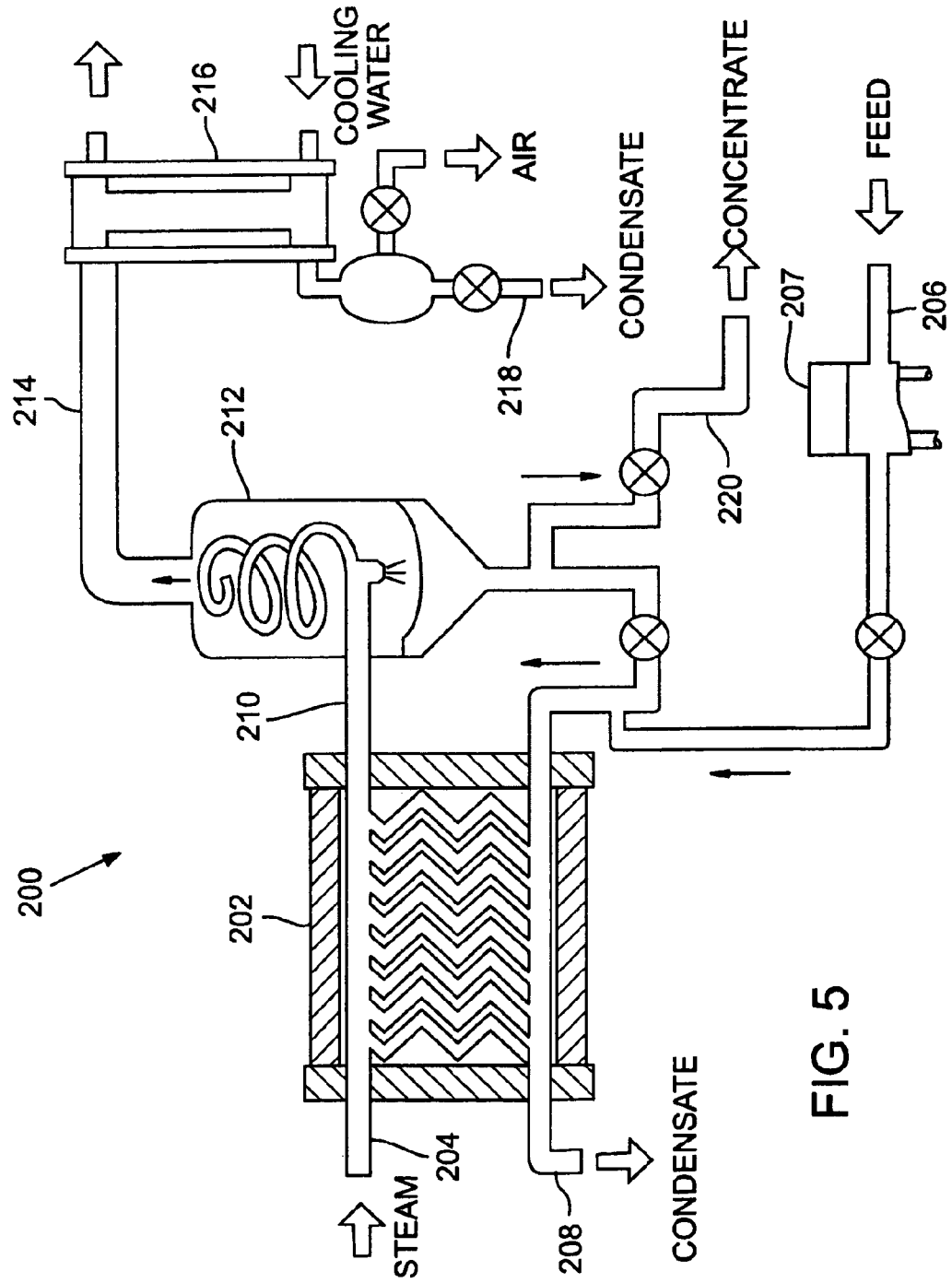
FIG. 5 is a diagram of an advantageous type of evaporator.

In an alternative embodiment a "paraflash" evaporator or similar evaporator system (http://www.apv.com/us/eng/technologies/evaporation/Evaporation.asp) from APV Corporation, instead of the evaporator system shown in FIG. 2. An example system 200 is shown in FIG. 5, which depicts the plate pack (evaporator) 202 that is supplied both with steam 204 and with a feed stream 206 of material to be concentrated. The feed stream 206 can include a solids trap 207. The plate pack 202 comprises steam compartments and feed-stream compartments configured to perform heat exchange between the compartments. As the steam passes through the steam compartments, some of the steam is condensed to condensate 208 from heat-exchange with the feed stream passing through the feed-stream compartments. The heat-exchange produces a stream of concentrated product 210 that is routed to a vapor separator 212. The vapor 214 from the vapor separator is routed to a condenser 216 in which a condensate 218 is produced. Meanwhile, concentrate 220 produced in the vapor separator 212 is drawn off for use in a downstream process.

Advantages of the evaporator system shown in FIG. 5 include fewer moving parts, less maintenance, and lower cost. The evaporator system employs suppressed boiling within its heated plate pack, allowing evaporation of water to occur in a vacuum separator. The paraflash evaporator can be used in single or multiple effects. Suppressed boiling along with high liquid velocities deter scaling on the heat-transfer surface of the plate pack, minimizing cleaning down-time and promoting longer production runs.

Dehydration of the suspension via passage through the evaporator system causes a portion of the partially hydrolysed protein to self-agglomerate into proteinaceous granules suspended in an oil medium. The material enters the oil-separation stage 50 of the process. In this stage, a controlled portion of the oils is removed from the suspension, yielding a stream of oil of which at least a portion can be recirculated to upstream of the heat exchanger. The oil-separation stage 50 also yields the final product 100 in a substantially dry, particulate form comprising partially hydrolysed, non-denatured animal protein.

Oil removal is preferably achieved by passing the suspension through an oil-separation centrifuge 102. As the suspension is fed into the centrifuge 102, a large portion of the oil is removed and passed out of the centrifuge 102 through a conduit 104 to a holding tank 106. As the oil is removed, the partially hydrolysed, non-denatured protein in the suspension is converted into the desired powdery granular product 100 which is also passed out of the centrifuge 102.

A portion of the oil collected in the holding tank 106 is withdrawn therefrom through a conduit 108 using a positive-displacement oil pump 110 which delivers the oil at a preset flow-rate into the temperature-controlled holding tank 31. Excess oil remaining in the holding tank 106 can be collected 112 for other commercial uses.

The amount of oil removed from the suspension by the centrifuge 102 is governed by variables such as the rotational speed, volumetric capacity, and maximum allowable throughput rate of the centrifuge 102. The amount of oil removed is also determined by the product itself, where a suspension having a relatively high moisture level (10% to 15%) will result in a relatively low product oil level (20% to 25%) and a suspension having a relatively low moisture level (6% to 10%) will result in a relatively high product oil level (30% to 35%). At a moisture content of less than 8% (w/w), passing the proteinaceous product out of the centrifuge 102 may be difficult.

The typical product 100 produced by the present method from fish residuals has a moisture content within a range of about 10% to about 15% (w/w), an oil content within a range of about 20% to about 35% (w/w), a protein content within a range of about 40% to 60% (w/w), and an ash content within a range of about 0% to about 7% (w/w). The relatively high oil content in contrast with other particulate high-protein products makes the product 100 generally more appealing to animals and seems to allow a higher moisture content than, for example, conventional fish meal without spoilage of the product 100. In other words, prior art fish meals containing almost no oil will usually exhibit substantial growth of molds and the like if the moisture content is above about 10%. (Typically, fish meals have a moisture content of about 6% to 8%). The product 100, in contrast, even while having a moisture level of about 13 percent, is relatively resistant to mold growth.

However, the main reason why the product 100 is believed to be more resistant to mold growth at a water content greater than about 10% is because the partially hydrolysed protein tends to tie up a substantial amount of water in a form unavailable for biological growth. This is in contrast with existing fish meals, comprised mostly of protein in a denatured (at least partially cooked) form which ties up less water. Tying up water is desirable not only because storability is improved but because the product also carries this water-binding capacity with it when added to or used as a feed, allowing a higher moisture content in the feed. A higher moisture level in a feed will often improve its acceptability by animals intended to consume the feed.

If desired, antioxidants and mold-inhibitors can be added to the product 100 for enhanced stability, especially for long-term storage or storage under particularly humid conditions. Representative antioxidants include butylated hydroxyanisole (BHA), butylated hydroxytoluene (BHT), and ethoxyquin. A representative mold-inhibitor is potassium sorbate.

The product 100 is also superior to existing fish meals and the like because of the low amount of ash therein. "Ash" denotes non-combustible mineral-laden residues derived principally from bones. Production of fish meal often does not include a bone-removal step.

The product 100 also has other advantages over conventional fish meal. Since most of the bone matter has been removed, the product 100 needs no further grinding. (Fish meal typically must be ground in a hammer mill or the like before the meal can be added to a feed.) Even when the product 100 has been pelletized, it can easily be broken up into a fine powder by simple agitation in a mixer. The product 100 also has the ability to bind ingredients of a feed together and thus reduces the need for expensive binders.

The product 100 derived from various animal sources is remarkably consistent with respect to the relative contents of moisture and oil. The oil content tends to be about double that of water, and the sum of the oil and water contents tends to be within the range of about 40 to 45% (w/w). This constancy is maintained automatically despite varying levels of fats, oils, and water in different types of raw animal matter used to make the product 100. Even in fish, the fat levels can vary appreciably, depending for example upon the species, the time of year when the fish were caught, and the water temperature. Nevertheless, product 100 made from different types of fish caught during different seasons consistently includes about 20% to 35% (w/w) oil and about 10% to 15% (w/w) water.

One reason for such constancy is that, as the moisture level changes, the oil content during processing will adjust accordingly to yield the same ratio. Also, the percentage w/w of oil and moisture appears to be dictated in part by the capability of the centrifuge 102, which operates satisfactorily within a level of about 8% to 20% moisture in the product. If too much water is present, the protein is insufficiently agglomerated into particles, resulting in partially hydrolysed protein tending to pass out of the suspension with the oil. If the moisture level is too low, the particles of partially hydrolysed protein tend to become too tightly packed in the centrifuge 102, resulting in too much oil remaining in the product and difficulty in passing the product out of the centrifuge 102.

The product 100 has a number of uses, depending in part on the type of animal from which the protein was derived. In general, it may be used as a high protein food additive, supplement, or nutraceutical, particularly for other animals such as pets, cattle, swine, and poultry. It may also be used alone, such as for feeding aquaculture-raised fish.

The product 100 has excellent storage properties and may be transported and stored in bulk quantities. Although the product is not hygroscopic, it is important to make sure that the moisture content be kept at about 10% to 15% (w/w) which is the normal endogenous moisture level of the product. Therefore, special precautions may have to be taken when transporting and storing in wet or humid environments to keep the product dry. Otherwise, no special atmospheric conditions for storage are required. Keeping the moisture level within endogenous levels prevents mold growth without needing to add mold inhibitors to the product.

Although the product is not sterile after manufacture, it is pasteurized, which means that substantially all harmful microorganisms have been eliminated therefrom.

Whereas the invention has been described in connection with preferred and alternative embodiments, it will be understood that it is not limited to those embodiments. On the contrary, it is intended to cover all alternatives, modifications, and equivalents as may be included within the spirit and scope of the invention as defined by the appended claims.

What is claimed is:

1. A method for preparing a proteinaceous product from raw protein-comprising animal matter, the method comprising:
   (a) providing the raw animal matter in a ground condition;
   (b) adding food grade oil to form an animal matter/oil suspension;
   (c) hydrolysing the proteins in the animal matter/oil suspension using proteolytic enzymes, where the hydrolysis is performed at a selected temperature within a range conducive for hydrolytic activity of the enzymes without denaturing the protein and for a time period sufficient to achieve a preselected degree of partial hydrolysis of the protein, to form a hydrolysate/oil suspension;
   (d) heating the hydrolysate/oil suspension to deactivate the proteolytic enzymes;
   (e) removing at least some non-digestible solids from the hydrolysate/oil suspension;
   (f) pasteurizing the hydrolysate/oil suspension;
   (g) reducing the concentration of water in the suspension; and
   (h) removing a portion of the oil from the suspension to form a particulate, partially hydrolysed, non-denatured proteinaceous product.

2. The method of claim 1, wherein step (a) comprises comminuting the raw animal matter.

3. The method of claim 1, wherein step (b) further comprises adding extraneous hydrolytic enzymes to the oil before adding the oil to the animal matter.

4. The method of claim 3, further comprising pre-heating the food-grade oil to a temperature within the range before or during step (b).

5. The method of claim 1, further comprising preheating the ground animal matter after step (a) but before step (c) to elevate the temperature thereof to within the range conducive for hydrolytic activity of the enzymes without causing denaturation of the protein.

6. The method of claim 5, wherein the ground animal matter is preheated to a temperature, within the range, of about 140° F. to 150'F.

7. The method of claim 5, wherein the ground animal matter is preheated concurrently with the adding of supplementary proteolytic enzymes and food grade oil at step (b).

8. The method of claim 7, wherein the supplementary proteolytic enzymes and food grade oil added at step (b) are preheated to a temperature, within the range, of about 140° F. to 150° F.

9. The method of claim 7, wherein the animal matter/oil suspension is preheated by passing the ground animal matter through a heat exchanger.

10. The method of claim 9, wherein the heat exchanger is a hybrid shell and tube heat exchanger with no moving parts.

11. The method of claim 9, wherein step (c) comprises passing the preheated animal matter/oil suspension through at least one digester in which the proteolytic enzymes partially hydrolyse the proteins in the ground animal matter.

12. The method of claim 11, wherein both preheating the animal matter/oil suspension and step (c) are performed in the heat exchanger.

13. The method of claim 11, wherein the preselected degree of partial protein hydrolysis is achieved by passing the preheated animal matter/oil/enzyme suspension through the at least one digester at a controlled flow-rate in a plug-flow manner.

14. The method of claim 1, wherein in step (d) the hydrolysate/oil suspension is heated to a temperature within a range of about 174° F. to about 200° F. to deactivate the enzymes.

15. The method of claim 14, wherein the enzymes are deactivated by injecting steam into the hydrolysate/oil suspension.

16. The method of claim 14, wherein the enzymes are deactivated by passing the hydrolysate/oil suspension through a heat exchanger.

17. The method of claim 1, wherein step (e) is performed using a centrifuge.

18. The method of claim 1, wherein in step (b) the food grade oil comprises a portion of the oil removed in step (h).

19. The method of claim 1, wherein step (g) is performed using multi-effect evaporators.

20. A particulate proteinaceous product, prepared by the method recited in claim 1.

21. A method for preparing a particulate proteinaceous product comprising partially hydrolysed animal protein from raw animal matter, the method comprising:
   reducing raw animal matter to a ground condition;
   adding a food grade oil-enzyme mixture comprising at least one type of proteolytic enzymes to the ground animal matter to form a pre-digestion mixture;
   preheating the pre-digestion mixture to a digestion temperature, of at least 20° C. and within a range suitable for proteolytic activity of the enzymes without denaturing the proteins in the pre-digestion mixture;

maintaining the mixture at said digestion temperature while the enzymes partially hydrolyse the proteins in the mixture, to form a hydrolysate/oil suspension;
heat-inactivating the enzymes;
separating and removing solids from the hydrolysate/oil suspension;
removing at least some water from the suspension; and
removing at least some oil from the suspension until the concentration of remaining oil is within a range of about 20 to 35 w/w percent and the concentration of partially hydrolysed animal protein in said product is within a range of about 45 to about 65 w/w percent.

22. A particulate proteinaceous product, prepared by the method recited in claim 21.

\* \* \* \* \*